(12) United States Patent
Ahmed et al.

(10) Patent No.: US 8,063,118 B2
(45) Date of Patent: *Nov. 22, 2011

(54) SUPERABSORBENT POLYMER COMPOSITIONS HAVING COLOR STABILITY

(75) Inventors: Iqbal Ahmed, Greensboro, NC (US); Mirko Walden, Herten (DE); Brian King, Greensboro, NC (US); Scott J. Smith, Greensboro, NC (US); Harald Schmidt, Toenisvorst (DE)

(73) Assignee: Evonik Stockhausen, LLC, Greensboro, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/884,713

(22) Filed: Sep. 17, 2010

(65) Prior Publication Data

US 2011/0009841 A1    Jan. 13, 2011

Related U.S. Application Data

(63) Continuation of application No. 11/778,372, filed on Jul. 16, 2007, now Pat. No. 7,816,426.

(51) Int. Cl.
*A61F 13/15* (2006.01)
*C08K 9/00* (2006.01)

(52) U.S. Cl. ........ 523/200; 523/201; 524/157; 524/167; 524/421; 604/370

(58) Field of Classification Search .................. 523/200, 523/201; 524/157, 167, 421; 604/370
See application file for complete search history.

(56) References Cited

U.S. PATENT DOCUMENTS

| 4,076,663 | A | 2/1978 | Masuda et al. |
| 4,131,576 | A | 12/1978 | Iovine et al. |
| 4,179,367 | A | 12/1979 | Barthell et al. |
| 4,286,082 | A | 8/1981 | Tsubakimoto et al. |
| 4,340,706 | A | 7/1982 | Obayashi et al. |
| 4,587,308 | A | 5/1986 | Makita et al. |
| 4,863,989 | A | 9/1989 | Obayashi et al. |
| 5,180,804 | A | 1/1993 | Niessner et al. |
| 5,409,771 | A | 4/1995 | Dahmen et al. |
| 5,451,613 | A | 9/1995 | Smith et al. |
| 5,462,972 | A | 10/1995 | Smith et al. |
| 5,610,220 | A | 3/1997 | Klimmek et al. |
| 5,672,633 | A | 9/1997 | Brehm et al. |
| 5,712,316 | A | 1/1998 | Damhen et al. |
| 5,773,542 | A * | 6/1998 | Koudate et al. ............... 526/215 |
| 6,060,557 | A | 5/2000 | Dahmen et al. |
| 6,211,400 | B1 | 4/2001 | Berghofer et al. |

(Continued)

FOREIGN PATENT DOCUMENTS

CA    2460152 A1    3/2003
(Continued)

OTHER PUBLICATIONS

Ahmed et al., U.S. Appl. No. 11/778,713, filed Jul. 16, 2007, Final Office Action dated Jul. 23, 2010.
(Continued)

*Primary Examiner* — Peter D Mulcahy
(74) *Attorney, Agent, or Firm* — Smith Moore Leatherwood LLP; Philip P. McCann

(57) ABSTRACT

The invention relates to absorptive, crosslinked polymeric compositions that are based on partly neutralized, monoethylenically unsaturated monomer carrying acid groups wherein the absorptive, crosslinked polymeric composition further includes an antioxidant and is color stable.

21 Claims, 3 Drawing Sheets

U.S. PATENT DOCUMENTS

| | | |
|---|---|---|
| 6,359,049 B1 | 3/2002 | Carrico et al. |
| 6,403,700 B1 | 6/2002 | Dahmen et al. |
| 6,906,131 B2 | 6/2005 | Ahmed et al. |
| 7,163,969 B2 | 1/2007 | Ahmed et al. |
| 7,169,843 B2 | 1/2007 | Smith et al. |
| 7,173,086 B2 | 2/2007 | Smith et al. |
| 7,241,820 B2 | 7/2007 | Smith et al. |
| 7,244,812 B2 | 7/2007 | Muller et al. |
| 7,291,674 B2 | 11/2007 | Kang et al. |
| 7,312,286 B2 | 12/2007 | Lang et al. |
| 7,335,713 B2 | 2/2008 | Lang et al. |
| 7,399,813 B2 | 7/2008 | Lang et al. |
| 7,427,650 B2 | 9/2008 | Smith et al. |
| 7,482,058 B2 | 1/2009 | Ahmed et al. |
| 7,488,541 B2 | 2/2009 | Ahmed et al. |
| 7,541,395 B2 | 6/2009 | Reimann et al. |
| 7,579,402 B2 | 8/2009 | Ahmed et al. |
| 7,625,957 B2 | 12/2009 | Harren et al. |
| 7,777,093 B2 | 8/2010 | Smith et al. |
| 7,795,345 B2 | 9/2010 | Smith et al. |
| 2006/0029782 A1 | 2/2006 | Harren et al. |
| 2006/0074160 A1 | 4/2006 | Handa et al. |
| 2006/0229369 A1* | 10/2006 | Frank et al. .......... 516/155 |
| 2007/0066754 A1 | 3/2007 | Loeker et al. |
| 2007/0135554 A1 | 6/2007 | McIntosh et al. |
| 2007/0260357 A1 | 11/2007 | Issberner et al. |
| 2008/0009616 A1 | 1/2008 | Frank et al. |
| 2008/0214740 A1 | 9/2008 | Harren et al. |
| 2008/0221277 A1 | 9/2008 | Walden et al. |
| 2008/0234420 A1 | 9/2008 | Smith et al. |
| 2008/0280128 A1 | 11/2008 | Furno et al. |
| 2009/0023848 A1 | 1/2009 | Ahmed et al. |
| 2009/0105389 A1 | 4/2009 | Walden et al. |
| 2009/0134357 A1 | 5/2009 | Bub et al. |
| 2009/0191408 A1 | 7/2009 | Tian et al. |
| 2009/0202805 A1 | 8/2009 | Furno et al. |
| 2009/0227741 A1 | 9/2009 | Walden et al. |
| 2010/0035757 A1 | 2/2010 | Furno et al. |
| 2010/0057027 A1 | 3/2010 | Furno et al. |
| 2010/0075844 A1 | 3/2010 | Loeker et al. |
| 2010/0099781 A1 | 4/2010 | Tian et al. |
| 2010/0100066 A1 | 4/2010 | Azad et al. |
| 2010/0130355 A1 | 5/2010 | Tian et al. |
| 2010/0209379 A1 | 8/2010 | Furno et al. |

FOREIGN PATENT DOCUMENTS

| | | |
|---|---|---|
| CN | 02819951 | 8/2007 |
| DE | 2706135 A1 | 8/1978 |
| DE | 2840010 A1 | 6/1979 |
| DE | 3503458 A1 | 8/1985 |
| DE | 3713601 A1 | 11/1988 |
| DE | 4020780 C1 | 8/1991 |
| DE | 4244548 A1 | 7/1994 |
| DE | 4418818 A1 | 1/1995 |
| DE | 4333056 A1 | 3/1995 |
| DE | 19529348 A1 | 2/1997 |
| DE | 10249821 A1 | 5/2004 |
| DE | 10334286 A1 | 3/2005 |
| EP | 0412363 A2 | 2/1991 |
| EP | 0505163 A1 | 9/1992 |
| EP | 1438354 A1 | 7/2004 |
| WO | 9605234 A1 | 2/1996 |
| WO | 9934843 A1 | 7/1999 |
| WO | 0055245 A1 | 9/2000 |
| WO | 02056812 A2 | 7/2002 |
| WO | 03025054 A1 | 3/2003 |
| WO | 2004022609 A1 | 3/2004 |
| WO | 2004037903 A2 | 5/2004 |
| WO | 2004084962 A1 | 10/2004 |
| WO | 2005054356 A1 | 6/2005 |
| WO | 2006109882 A1 | 10/2006 |
| WO | 2009011717 A1 | 1/2009 |

OTHER PUBLICATIONS

Ahmed et al., U.S. Appl. No. 11/778,713, filed Jul. 16, 2007, Office Action dated Feb. 3, 2010.

Ahmed et al., U.S. Appl. No. 11/778,713, filed Jul. 16, 2007, Office Action dated Apr. 6, 2009.

International Search Report mailed on Feb. 10, 2009 in PCT/EP2008/065123.

International Search Report mailed on Jul. 21, 2008 in PCT/US2007/089047.

Loeker et al., U.S. Appl. No. 12/882,594, filed Sep. 15, 2010.

Smith et al., U.S. Appl. No. 12/830,890, filed Jul. 6, 2010.

Smith et al., U.S. Appl. No. 12/851,664, filed Aug. 6, 2010.

Walden, U.S. Appl. No. 12/740,054, filed Jul. 23, 2010.

Written Opinion (German) mailed on Feb. 10, 2009 in PCT/EP2008/065123.

Written Opinion mailed on Aug. 7, 2008 in PCT/US2007/089047.

* cited by examiner

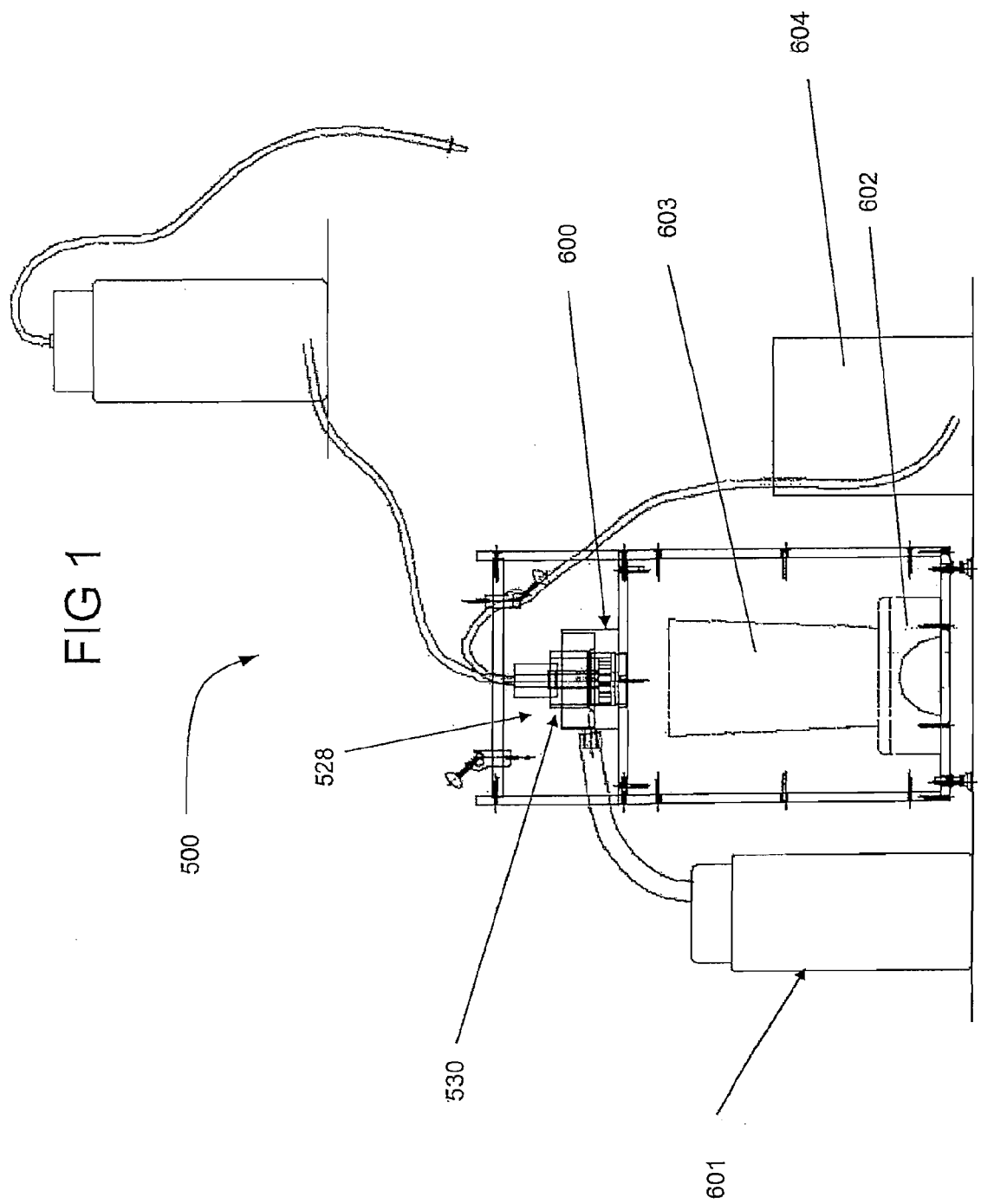

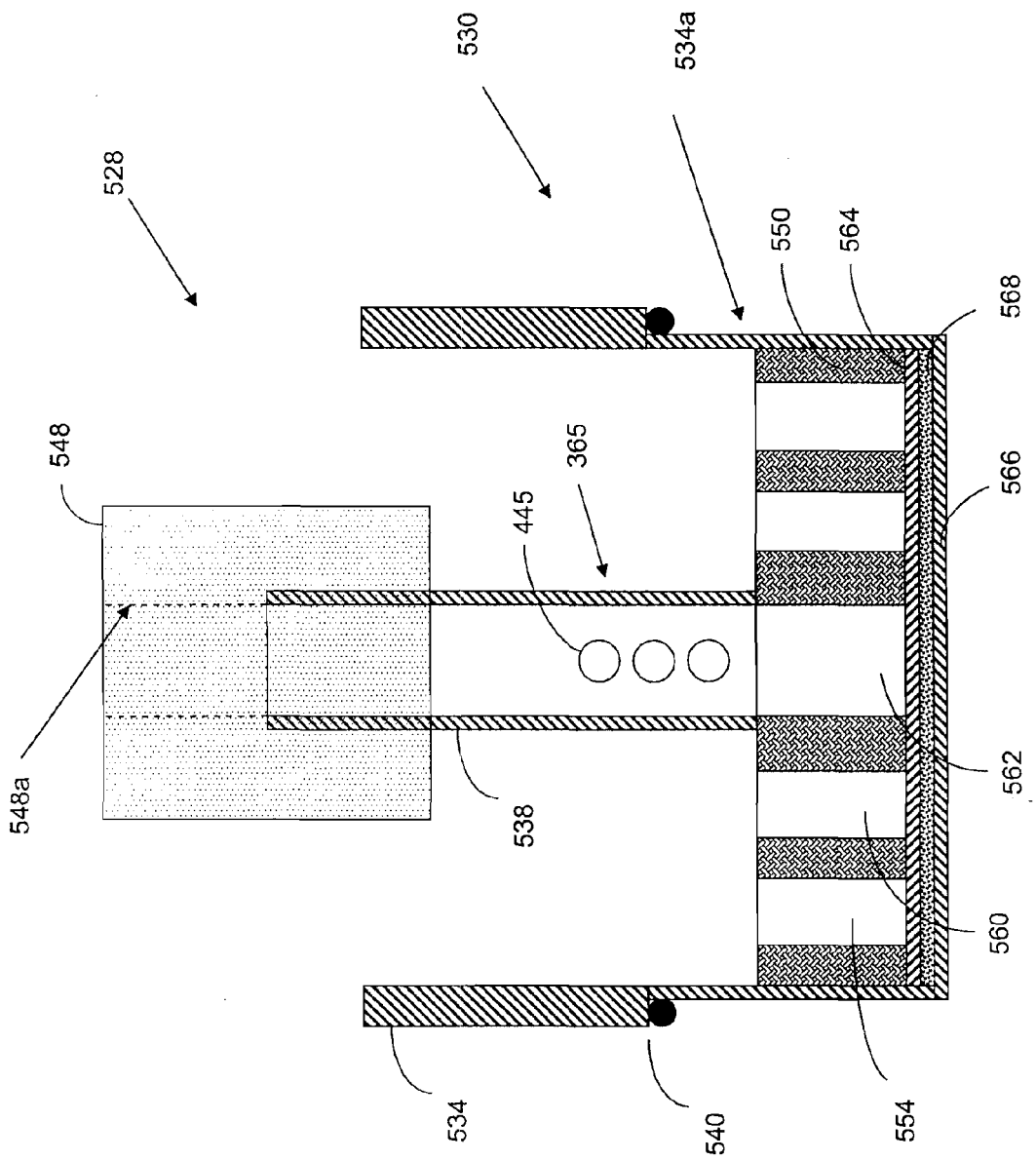

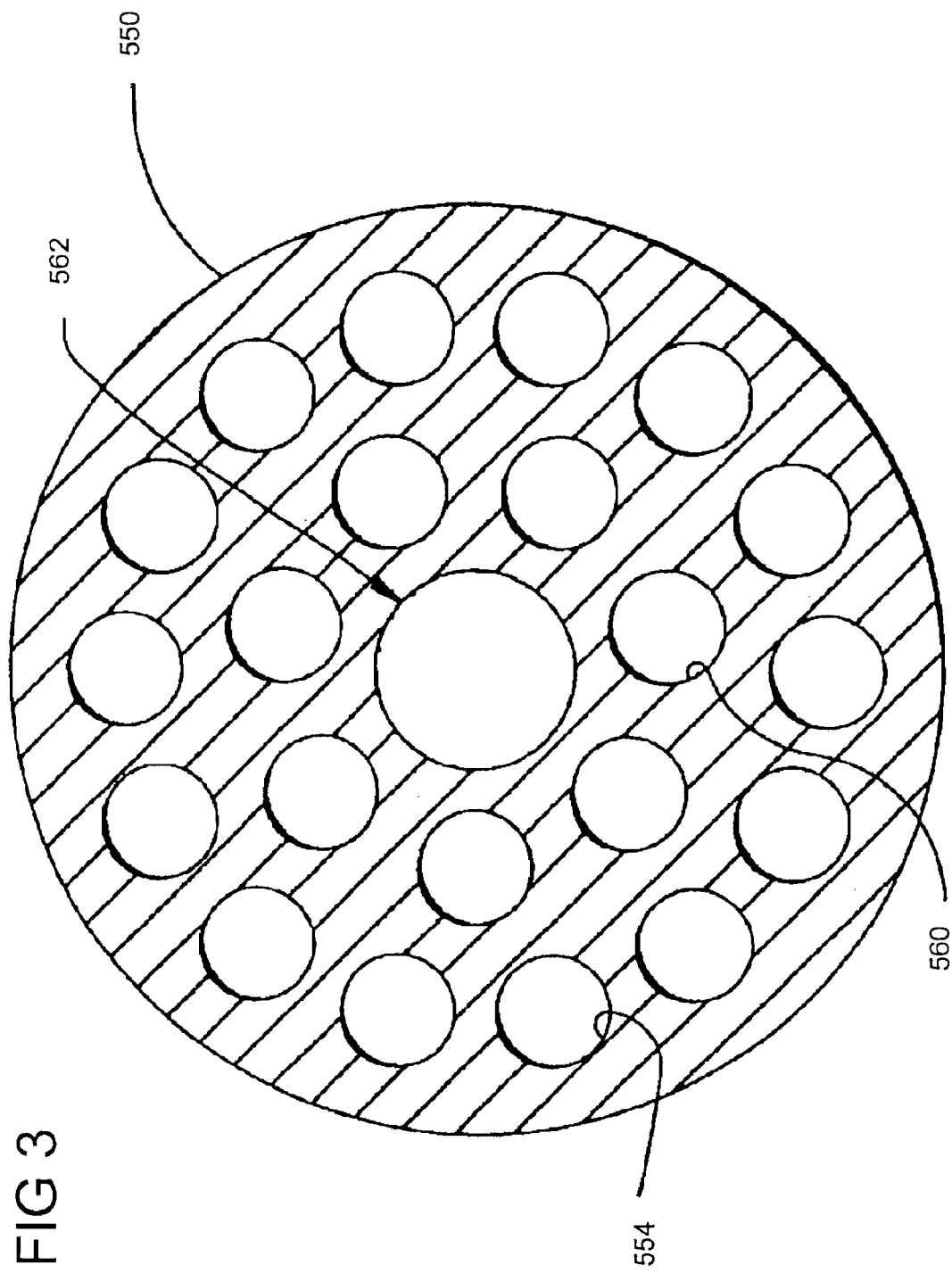

SUPERABSORBENT POLYMER COMPOSITIONS HAVING COLOR STABILITY

This application is a continuation application of U.S. application Ser. No. 11/778,372 filed on Jul. 16, 2007, now U.S. Pat. No. 7,816,426, the disclosure of which is expressly incorporated herein by reference.

BACKGROUND

A superabsorbent material in general refers to a water-swellable, water-insoluble, material capable of absorbing at least about 10 times its weight, and up to about 30 times or more its weight in an aqueous solution containing 0.9 weight percent sodium chloride solution in water. The present invention relates to superabsorbent polymer compositions which absorb water, aqueous liquids, and blood.

A superabsorbent polymer is a crosslinked partially neutralized polymer that is capable of absorbing large amounts of aqueous liquids and body fluids, such as urine or blood, with swelling and the formation of hydrogels, and of retaining them under a certain pressure in accordance with the general definition of superabsorbent material. Superabsorbent polymer compositions may include post-treatment of the superabsorbent polymer such as surface crosslinking, surface treatment, and other treatment. Superabsorbent polymer particles are particles of superabsorbent polymers or superabsorbent polymer compositions. The acronym SAP may be used in place of superabsorbent polymer, superabsorbent polymer composition, and particles herein. A comprehensive survey of superabsorbent polymer compositions, and their use and manufacture, is given in F. L. Buchholz and A. T. Graham (editors) in "Modern Superabsorbent Polymer Technology," Wiley-VCH, New York, 1998.

Commercially available superabsorbent polymer compositions include crosslinked polyacrylic acids or crosslinked starch-acrylic acid graft polymers, in which some of the carboxyl groups are neutralized with sodium hydroxide solution or potassium hydroxide solution. A primary use of superabsorbent polymer compositions is in sanitary articles, such as babies' diapers, incontinence products, or sanitary towels. For fit, comfort, and aesthetic reasons, and from environmental aspects, there is an increasing trend to make sanitary articles smaller and thinner. This is being accomplished by reducing the content of the high volume fluff fiber in these articles. To ensure a constant total retention capacity of body fluids in the sanitary articles, more superabsorbent polymer composition content is being used in these sanitary articles.

The present invention relates to superabsorbent polymer composition having long-term color stability, and to methods of preparing the color-stable superabsorbent polymer composition, in particular retaining a measurable whiteness.

SUMMARY

An embodiment of the present invention comprises at least a superabsorbent polymer composition comprising a superabsorbent polymer comprising a) from about 55% to about 99.9% by weight of the superabsorbent polymer of polymerizable unsaturated acid group containing monomer based on the superabsorbent polymer; and b) from about 0.001% to about 5% by weight of internal crosslinking agent based on the polymerizable unsaturated acid group containing monomer; c) from about 50 to 1000 ppm of a thermal initiator based on the polymerizable unsaturated acid group containing monomer; wherein the superabsorbent polymer has a degree of neutralization of greater than about 25%; wherein elements a), b), and c) are polymerized into a crosslinked hydrogel, which is then prepared into superabsorbent polymer particles; the superabsorbent polymer composition further comprising the following additives to form superabsorbent polymer composition particles, i) from about 0.001% to about 5% by weight of surface crosslinking agent based on the superabsorbent polymer composition; and wherein from about 0.01% to about 5% by weight of an antioxidant based on the superabsorbent polymer composition is added to the polymerized product whether in the crosslinked hydrogel, or subsequent superabsorbent polymer particles, or superabsorbent polymer composition form wherein the superabsorbent polymer composition has a free swell gel bed permeability of at least about 6 Darcy as measured by the Free Swell Gel Bed Permeability Test.

Numerous other features and advantages of the present invention will appear from the following description. In the description, reference is made to exemplary embodiments of the invention. Such embodiments do not represent the full scope of the invention. Reference should therefore be made to the claims herein for interpreting the full scope of the invention. In the interest of brevity and conciseness, any ranges of values set forth in this specification contemplate all values within the range and are to be construed as support for claims reciting any sub-ranges having endpoints which are real number values within the specified range in question. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

In addition, the present invention is directed to absorbent compositions or sanitary articles that may contain superabsorbent polymer compositions of the present invention.

FIGURES

The foregoing and other features, aspects, and advantages of the present invention will become better understood with regard to the following description, appended claims, and accompanying drawings where:

FIG. 1 is a side view of the test apparatus employed for the Free Swell Gel Bed Permeability Test;

FIG. 2 is a cross-sectional side view of a cylinder/cup assembly employed in the Free Swell Gel Bed Permeability Test apparatus shown in FIG. 1;

FIG. 3 is a top view of a plunger employed in the Free Swell Gel Bed Permeability Test apparatus shown in FIG. 1; and

DEFINITIONS

It should be noted that when employed in the present disclosure, the terms "comprises," "comprising," and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The term "absorbent article" generally refers to devices that can absorb and contain fluids. For example, personal care absorbent articles refer to devices that are placed against or near the skin to absorb and contain the various fluids discharged from the body.

The term "Darcy" is a CGS unit of permeability. One Darcy is the permeability of a solid through which one cubic centimeter of fluid, having a viscosity of one centipoise, will flow in one second through a section one centimeter thick and one square centimeter in cross-section, if the pressure difference between the two sides of the solid is one atmosphere. It turns out that permeability has the same units as area; since there is no SI unit of permeability, square meters are used. One Darcy is equal to about $0.98692 \times 10^{-12}$ m$^2$ or about $0.98692 \times 10^{-8}$ cm$^2$.

The term "disposable" is used herein to describe absorbent articles that are not intended to be laundered or otherwise restored or reused as an absorbent article after a single use. Examples of such disposable absorbent articles include, but are not limited to, personal care absorbent articles, health/medical absorbent articles, and household/industrial absorbent articles.

The term "crosslinked" used in reference to the superabsorbent polymer refers to any means for effectively rendering normally water-soluble materials substantially water-insoluble but swellable. Such a crosslinking means can include, for example, physical entanglement, crystalline domains, covalent bonds, ionic complexes and associations, hydrophilic associations such as hydrogen bonding, hydrophobic associations, or Van der Waals forces.

The term "dry superabsorbent polymer composition" generally refers to the superabsorbent polymer composition having less than about 10% moisture.

The terms "particle," "particulate," and the like, when used with the term "superabsorbent polymer," refer to the form of discrete units. The units can comprise flakes, fibers, agglomerates, granules, powders, spheres, pulverized materials, or the like, as well as combinations thereof. The particles can have any desired shape: for example, cubic, rod-like, polyhedral, spherical or semi-spherical, rounded or semi-rounded, angular, irregular, et cetera. Shapes having a high aspect ratio, like needles, flakes, and fibers, are also contemplated for inclusion herein. The terms "particle" or "particulate" may also include an agglomeration comprising more than one individual particle, particulate, or the like. Additionally, a particle, particulate, or any desired agglomeration thereof may be composed of more than one type of material.

The term "polymer" includes, but is not limited to, homopolymers, copolymers, for example, block, graft, random, and alternating copolymers, terpolymers, etc., and blends and modifications thereof. Furthermore, unless otherwise specifically limited, the term "polymer" shall include all possible configurational isomers of the material. These configurations include, but are not limited to isotactic, syndiotactic, and atactic symmetries.

The term "polyolefin" as used herein generally includes, but is not limited to, materials such as polyethylene, polypropylene, polyisobutylene, polystyrene, ethylene vinyl acetate copolymer, and the like, the homopolymers, copolymers, terpolymers, etc., thereof, and blends and modifications thereof. The term "polyolefin" shall include all possible structures thereof, which include, but are not limited to, isotatic, synodiotactic, and random symmetries. Copolymers include atactic and block copolymers.

The term "relative humidity" refers to the amount of water vapor in the air, as measured as the percent of saturation humidity and generally determined by the equation Relative humidity=[(actual vapor density)/(saturation vapor density)]×100%. For 40° C., the saturation vapor density is 51.1 g/cm$^3$, and the actual vapor density would be about 40.83 g/cm$^3$.

The term "superabsorbent materials" refers to water-swellable, water-insoluble organic or inorganic materials including superabsorbent polymers and superabsorbent polymer compositions capable, under the most favorable conditions, of absorbing at least about 10 times their weight, or at least about 15 times their weight, or at least about 25 times their weight in an aqueous solution containing 0.9 weight percent sodium chloride.

The term "superabsorbent polymer composition" refers to a superabsorbent polymer comprising a surface additive in accordance with the present invention.

The terms "superabsorbent polymer" and "superabsorbent polymer preproduct" refer to a material that is produced by conducting all of the steps for making a superabsorbent polymer as described herein, up to and including drying the material, and coarse grinding in a crusher.

The term "surface crosslinking" means that the level of functional crosslinks in the vicinity of the surface of the superabsorbent polymer particle generally is higher than the level of functional crosslinks in the interior of the superabsorbent polymer particle. As used herein, "surface" describes the outer-facing boundaries of the particle. For porous superabsorbent polymer particles, exposed internal surface also are included in the definition of surface.

The term "thermoplastic" describes a material that softens when exposed to heat and which substantially returns to a non-softened condition when cooled to room temperature.

The term "whiteness index" when used herein is to be interpreted as based on measurement of uniform color spaces on the CIE 1976 L*a*b* scale for any illuminant as recommended by the Commission Internationale de l'Eclairage (CIE). The CIE L*a*b* scale is a simplified cube root version of the Adams-Nickerson space produced by the quantities of CIE L*a*b* in rectangular coordinates. The relationship of the CIE L*a*b* scale and the CIE XYZ scale for any illuminant is described in the ASTM E 308 Standard Practice for Computing the Colors of Objects by Using the CIE System. From the measurement of the quantities of CIE L*a*b* using a Colorflex® Spectrocolorimeter (commercially available from Hunter Associates Laboratory in Reston, Va., USA,), the Whiteness Index in relationship with physical observation was derived as Whiteness Index=(L*/b*)–a*>7.5=Sample looks white, wherein L*–=dark, L*+=white; b*–=blue, b*+=yellow, a*–=green, and a*+=red. The theoretical "perfect white" has reference values of 100% across the visible spectrum with corresponding colorimetric values of L*=100.00, a*=0.00 and b*=0.00. An item near white, it may be darker, lower L* value, and possibly be slightly chromatic either in the red-green dimension (a*) of in the yellow-blue dimension (b*).

The term "% by weight" or "% wt" when used herein and referring to components of the superabsorbent polymer composition, is to be interpreted as based on the weight of the dry superabsorbent polymer composition, unless otherwise specified herein.

These terms may be defined with additional language in the remaining portions of the specification.

DETAILED DESCRIPTION

An embodiment of the present invention includes a superabsorbent polymer composition comprising superabsorbent polymer particles surface treated with from about 0.01% to about 5% by weight of an antioxidant compound, based on the superabsorbent polymer composition wherein the antioxidant may be added to the polymerized product whether in crosslinked hydrogel or subsequent superabsorbent polymer particles or superabsorbent polymer composition form.

Another embodiment of the present invention includes a superabsorbent polymer composition comprising a superabsorbent polymer comprising:

a) from about 55% to about 99.9% by weight of the superabsorbent polymer of polymerizable unsaturated acid group containing monomers based on the superabsorbent polymer; and b) from about 0.001% to about 5% by weight of internal crosslinking agent based on the polymerizable unsaturated acid group containing monomer, c) from about 50 to 1000 ppm of a thermal initiator based on the polymerizable unsaturated acid group containing monomer;

wherein the superabsorbent polymer has a degree of neutralization of greater than about 25%; wherein elements a), b) and c) are polymerized into a crosslinked hydrogel, which is then prepared into superabsorbent polymer particles; the superabsorbent polymer composition further comprising the following additives to form superabsorbent polymer composition particles i) from about 0.001% to about 5% by weight of surface crosslinking agent based on the superabsorbent polymer composition; and wherein from about 0.01% to about 5% by weight of an antioxidant based on the superabsorbent polymer composition is added to the polymerized product whether in crosslinked hydrogel or subsequent superabsorbent polymer particles or superabsorbent polymer composition particle form wherein the superabsorbent polymer composition has a free swell gel bed permeability of at least about 6 Darcy as measured by the Free Swell Gel Bed Permeability Test.

A superabsorbent polymer as set forth in embodiments of the present invention is obtained by the initial polymerization of from about 55% to about 99.9% by weight of the superabsorbent polymer of polymerizable unsaturated acid group containing monomer. A suitable monomer includes any of those containing carboxyl groups, such as acrylic acid, methacrylic acid, or 2-acrylamido-2-methylpropanesulfonic acid, or mixtures thereof. It is desirable for at least about 50% by weight, and more desirable for at least about 75% by weight of the acid groups to be carboxyl groups.

The acid groups are neutralized to the extent of at least about 25 mol %, that is, the acid groups are desirably present as sodium, potassium, or ammonium salts. In some aspects, the degree of neutralization may be at least about 50 mol %. In some aspects, it is desirable to utilize polymers obtained by polymerization of acrylic acid or methacrylic acid, the carboxyl groups of which are neutralized to the extent of from about 50 mol % to about 80 mol %, in the presence of internal crosslinking agents.

In some aspects, the suitable monomer that can be copolymerized with the ethylenically unsaturated monomer may include, but is not limited to acrylamide, methacrylamide, hydroxyethyl acrylate, dimethylaminoalkyl(meth)-acrylate, ethoxylated (meth)-acrylates, dimethylaminopropylacrylamide, or acrylamidopropyltrimethylammonium chloride. Such monomer may be present in a range of from 0% to about 40% by weight of the copolymerized monomer.

The superabsorbent polymer of the invention also includes internal crosslinking agents. The internal crosslinking agent has at least two ethylenically unsaturated double bonds, or one ethylenically unsaturated double bond and one functional group that is reactive toward acid groups of the polymerizable unsaturated acid group containing monomer, or several functional groups that are reactive towards acid groups can be used as the internal crosslinking component and is desirably present during the polymerization of the polymerizable unsaturated acid group containing a monomer.

Examples of internal crosslinking agents include, but are not limited to, aliphatic unsaturated amides, such as methylenebisacryl- or -methacrylamide or ethylenebisacrylamide; aliphatic esters of polyols or alkoxylated polyols with ethylenically unsaturated acids, such as di(meth)acrylates or tri(meth)acrylates of butanediol or ethylene glycol, polyglycols or trimethylolpropane; di- and triacrylate esters of trimethylolpropane which may be oxyalkylated, desirably ethoxylated, with about 1 to about 30 moles of alkylene oxide; acrylate and methacrylate esters of glycerol and pentaerythritol and of glycerol and pentaerythritol oxyethylated with desirably about 1 to about 30 mol of ethylene oxide; allyl compounds, such as allyl(meth)acrylate, alkoxylated allyl (meth)acrylate reacted with desirably about 1 to about 30 mol of ethylene oxide, triallyl cyanurate, triallyl isocyanurate, maleic acid diallyl ester, poly-allyl esters, tetraallyloxyethane, triallylamine, tetraallylethylenediamine, diols, polyols, hydroxy allyl or acrylate compounds and allyl esters of phosphoric acid or phosphorous acid; and monomers that are capable of crosslinking, such as N-methylol compounds of unsaturated amides, such as of methacrylamide or acrylamide, and the ethers derived therefrom. Ionic crosslinkers such as multivalent metal salts may also be employed. Mixtures of the crosslinking agents mentioned can also be employed. The content of the internal crosslinking agents is from about 0.001% to about 5% by weight such as from about 0.2% to about 3% by weight based on the total amount of the polymerizable unsaturated acid group containing monomer.

The superabsorbent polymer composition of the invention may also include from about 50 to 1000 ppm of a thermal initiator based on the polymerizable unsaturated acid group containing monomer. Thermal initiators may include persulfates such as sodium persulfate, potassium persulfate, and ammonium persulfate; peroxides such as benzoyl peroxide, t-butyl peroxide, and methyl ethyl ketone peroxide; peroxyesters such as t-butylperoxypivalate, t-amylperoxypivalate, t-amylperoxy-2-ethylhexanoate and t-butylperoxyisobutyrate; and azo compounds such as azonitrile compounds, azoamidine compounds, cyclic azoamidine compounds, azoamide compounds, alkylazo compounds, 2,2'-azobis(2-amidinopropane)dihydrochloride, and 2,2'-azobis(2-(2-imidazolin-2-yl)propane)dihydrochloride.

In some aspects, initiators can be used for initiation of the free-radical polymerization. Suitable initiators include, but are not limited to, azo or peroxo compounds, redox systems or UV initiators, sensitizers, and/or radiation.

After polymerization, the superabsorbent polymer becomes a crosslinked hydrogel which is then prepared into superabsorbent polymer particles. The superabsorbent polymer particles may then be surface crosslinked by the addition of a surface crosslinking agent and heat-treatment. In general, surface crosslinking is a process that is believed to increase the crosslink density of the polymer matrix in the vicinity of the superabsorbent particle surface with respect to the crosslinking density of the particle interior.

In some particular aspects, desirable surface crosslinking agents include chemicals with one or more functional groups that are reactive toward pendant groups of the polymer chains, typically the acid groups. The surface crosslinking agent may be present in an amount of from about 0.001% to about 5% by weight of the dry superabsorbent polymer composition, and such as from about 0.1% to about 3% by weight, and such as from about 0.1% to about 1% by weight, based on the weight of the dry superabsorbent polymer composition. Applicants have found that a heat treatment step after addition of the surface crosslinking agent is desirable.

Surface crosslinking agents are chemical compounds that may contain functional groups capable of reacting with carboxylic acid or carboxyl groups. Surface crosslinking agents may include two functional groups such as some alcohol, amine, aldehyde, and carbonate groups may be used. Crosslinker molecules having multiple different functions may also be employed, such as polyols, polyamines, polyaminoalcohols, and alkylene carbonates. Ethylene glycol, diethylene glycol, triethylene glycol, polyethylene glycol, glycerol, polyglycerol, propylene glycol, diethanolamine, triethanolamine, polypropylene glycol, block copolymers of ethylene oxide and propylene oxide, sorbitan fatty acid esters, ethoxylated sorbitan fatty acid esters, trimethylolpropane, ethoxylated trimethylolpropane, pentaerythritol, ethoxylated pentaerythritol, polyvinyl alcohol, sorbitol, ethylene carbonate, propylene carbonate may be used. Polyols and ethylene carbonate may be used as surface crosslinking agents.

Surface crosslinking agents may be an alkylene carbonate followed by heating to effect surface crosslinking, which can improve the surface crosslinking density and the gel strength characteristics of the superabsorbent polymer particle. More specifically, the surface crosslinking agent is coated onto the superabsorbent polymer particulate by mixing the polymer particulate with an aqueous alcoholic solution of the alkylene carbonate surface crosslinking agent. The amount of alcohol is determined by the solubility of the alkylene carbonate and is kept as low as possible for various reasons. Suitable alcohols are methanol, isopropanol, ethanol, butanol, or butyl glycol, as well as mixtures of these alcohols. In some aspects, the solvent desirably is water, which typically is used in an amount of about 0.3% by weight to about 5.0% by weight, based on the weight of the dry superabsorbent polymer. In other aspects, the alkylene carbonate surface crosslinking agent is dissolved in water without any alcohol. In still other aspects, the alkylene carbonate surface crosslinking agent may be applied from a powder mixture, for example, with an inorganic carrier material, such as silicone dioxide ($SiO_2$), or in a vapor state by sublimation of the alkylene carbonate.

To achieve the desired surface crosslinking properties, the alkylene carbonate is distributed evenly on the particulate superabsorbent polymer. For this purpose, mixing is effected in suitable mixers known in the art, such as fluidized bed mixers, paddle mixers, rotary drum mixers, or twin-worm mixers. It is also possible to carry out the coating of the particulate superabsorbent polymer during one of the process steps in the production of the particulate superabsorbent polymer. In one particular aspect, a suitable process for this purpose is the inverse suspension polymerization process.

The heat treatment, that may follow the coating treatment, may be carried out as follows. In general, the heat treatment is at a temperature of from about 100° C. to about 300° C. Lower temperatures are possible if highly reactive epoxide crosslinking agents are used. However, if alkylene carbonates are used, then the thermal treatment is suitably at a temperature of from about 150° C. to about 250° C. In this particular aspect, the treatment temperature depends on the dwell time and the kind of alkylene carbonate. For example, at a temperature of about 150° C., the thermal treatment is carried out for one hour or longer. In contrast, at a temperature of about 250° C., a few minutes (e.g., from about 0.5 minutes to about 5 minutes) are sufficient to achieve the desired surface crosslinking properties. The thermal treatment may be carried out in conventional dryers or ovens known in the art.

The superabsorbent polymer composition of the invention may further include from about 0.01% to about 5% by weight of an antioxidant based on the superabsorbent polymer composition that may be added to the polymerized product whether in crosslinked hydrogel or subsequent superabsorbent polymer particles or superabsorbent polymer composition particle form. The antioxidant may be selected from a sulfite or bisulfite of an alkali metal, ammonium sulfite, sodium metabisulfite, ammonium bisulfite, sulfinic acid, 2-hydroxy-2-sulfinatoacetic acid, 2-hydroxy-2-sulfonatoacetic acid, 2-hydroxy-2-sulfonatoacetic acid, sulfamic acid, or sulfonic acid, and salts and derivatives of the foregoing. 2-Hydroxy-2-sulfinatoacetic acid and 2-hydroxy-2-sulfonatoacetic acid in sodium salt forms (a pure form), in combination with sodium bisulfite are available commercially from Bruggemann Chemical, Heilbron, Germany, as BRUGGOLITE® FF6 and BRUGGOLITE® FF7 reducing agents. 2-Hydroxy-2-sulfinatoacetic acid derivatives are disclosed in example 3 of U.S. Pat. No. 6,211,400, wherein example 3 of U.S. Pat. No. 6,211,400, is incorporated herein by reference.

The superabsorbent polymer composition of the invention may include up to about 1% by weight of the dry superabsorbent polymer composition of a chelating agent. The chelating agent used in the present invention includes, for example, an aminocarboxylic acid metal chelating agent such as iminodiacetic acid, hydroxyethyl iminodiacetate, nitrilotriacetic acid, nitrilotripropionic acid, ethylenediaminetetraacetic acid, diethylenetriaminepentaacetic acid, pentasodium diethylenetriaminepentaacetate, triethylenetetraminehexaacetic acid, trans-1,2-diaminocyclohexanetetraacetic acid, N,N-bis (2-hydroxyethyl)glycine, diaminopropanoltetraacetic acid, ethylenediaminedipropionic acid, hydroxyethylenediaminetriacetic acid, glycoletherdiaminetetraacetic acid, diaminopropanetetraacetic acid, N,N'-bis(2-hydroxybenzyl)ethylenediamine-N,N-diacetic acid, 1,6-hexamethylenediamine-N,N,N',N'-tetraacetic acid and salts thereof; a polyphosphoric acid metal chelating agent such as pyrophosphoric acid, tripolyphosphoric acid, tetrapolyphosphoric acid, trimetaphosphoric acid, tetrametaphosphoric acid, and salts thereof. Chelating agents may be a pentasodium diethylenetriaminepentaacetate such as Versenex®80 chelating agent that is commercially available from The Dow Chemical Company. Versenex®80 chelating agent is an aqueous solution of the pentasodium salt of diethylenetriaminepentaacetic acid.

The superabsorbent polymer composition of the present invention may include from 0 to about 5 wt % of a multivalent metal salt on the surface of the polymer, based on the weight of the dry superabsorbent polymer composition. The multivalent metal salt is preferably water soluble. Examples of preferred metal cations include the cations of Al, Fe, Zr, Mg and Zn. Preferably, the metal cation has a valence of at least +3, with Al being most preferred. Examples of preferred anions in the multivalent metal salt include halides, chlorohydrates, sulfates, lactate, nitrates and acetates. Examples of such multivalent metal salts include aluminium sulfate, and aluminum lactate. A form of aluminum sulfate is hydrated aluminum sulfate, preferably aluminum sulfate having from 12 to 14 waters of hydration. Mixtures of multivalent metal salts may be employed.

The polymer and multivalent metal salt suitably are mixed by dry blending, or preferably in solution, using means well known to those skilled in the art. Aqueous solutions are preferred. With dry blending, a binder may be employed in an amount which is sufficient to ensure that a substantially uniform mixture of the salt and the superabsorbent polymer is maintained. The binder may be water or a nonvolatile organic compound having a boiling point of at least 150° C. Examples of binders include water, polyols such as propylene glycol, glycerin and poly(ethylene glycol).

In some aspects, the superabsorbent polymer composition of the present invention may include up to about 5% by weight, and from about 0.001% to about 5% by weight, and from about 0.01% to about 0.5% by weight of the dry superabsorbent polymer composition of a polymeric coating, such as a thermoplastic coating, or a cationic coating, or a combination of a thermoplastic coating and a cationic coating. In some particular aspects, the polymeric coating desirably is a polymer that may be in a solid, emulsion, suspension, colloidal, or solubilized state, or combinations thereof. Polymeric coatings suitable for this invention may include, but are not limited to, a thermoplastic coating having a thermoplastic melt temperature wherein the polymeric coating is applied to the particle surface coincident with or followed by a temperature of the treated superabsorbent polymer particle at about the thermoplastic melt temperature.

Examples of thermoplastic polymers include, but are not limited to, polyolefin, polyethylene, polyester, polyamide, polyurethane, styrene polybutadiene, linear low density polyethylene (LLDPE), ethylene acrylic acid copolymer (EAA), ethylene alkyl methacrylate copolymer (EMA), polypropylene (PP), maleated polypropylene, ethylene vinyl acetate copolymer (EVA), polyester, polyamide, and blends of all families of polyolefins, such as blends of PP, EVA, EMA, EEA, EBA, HDPE, MDPE, LDPE, LLDPE, and/or VLDPE, may also be advantageously employed. The term polyolefin as used herein is defined above. A thermoplastic polymer may be functionalized to have additional benefits such as water solubility or dispersability.

Polymeric coatings of this invention may also include a cationic polymer. A cationic polymer as used herein refers to a polymer or mixture of polymers comprising a functional group or groups having a potential of becoming positively charged ions upon ionization in an aqueous solution. Suitable functional groups for a cationic polymer include, but are not limited to, primary, secondary, or tertiary amino groups, imino groups, imido groups, amido groups, and quaternary ammonium groups. Examples of synthetic cationic polymers include, but are not limited to, the salts or partial salts of poly(vinyl amines), poly(allylamines), poly(ethylene imine), poly(amino propanol vinyl ethers), poly(acrylamidopropyl trimethyl ammonium chloride), poly(diallyldimethyl ammonium chloride). Poly(vinyl amines) include, but are not limited to, LUPAMIN® 9095 available from BASF Corporation, Mount Olive, N.J. Examples of natural-based cationic polymers include, but are not limited to, partially deacetylated chitin, chitosan, and chitosan salts. Synthetic polypeptides such as polyasparagins, polylysines, polyglutamines, and polyarginines are also suitable cationic polymers.

The superabsorbent polymer compositions according to the invention may include from 0 to about 5 wt %, or from 0.05 to about 2.0 wt %, of a multivalent metal salt, based on the dry superabsorbent polymer composition. The multivalent metal salt may be applied to the surface of the superabsorbent polymer composition. The multivalent metal salt is preferably water soluble. Examples of preferred metal cations include the cations of Al, Fe, Zr, Mg and Zn. Preferably, the metal cation has a valence of at least +3, with Al being most preferred. Examples of preferred anions in the multivalent metal salt include halides, chlorohydrates, sulfates, lactates, nitrates and acetates, with chlorides, sulfates, chlorohydrates and acetates being preferred, chlorohydrates and sulfates being more preferred and sulfates being the most preferred. Aluminium sulfate is the most preferred multivalent metal salt and is readily commercially available. The multivalent metal salt may be aluminum sulfate such as hydrated aluminum sulfate, such as aluminum sulfate having from 12 to 14 waters of hydration. The multivalent metal salt may be aluminum lactate. Mixtures of multivalent metal salts can be employed.

The superabsorbent polymer compositions according to the invention may include from about 0.01% to about 2% by weight or from about 0.01% to about 1% by weight based on the dry superabsorbent polymer composition of a water-insoluble inorganic metal compound. The water-insoluble inorganic metal compound may be applied to the surface of the superabsorbent polymer composition. The water-insoluble inorganic metal compound may include, but are not limited to, a cation selected from aluminum, titanium, calcium, or iron and an anion selected from phosphate, borate, or chromate. Examples of water-insoluble inorganic metal compounds include aluminum phosphate and an insoluble metal borate. The insoluble metal borate is selected from titanium borate, aluminum borate, iron borate, magnesium borate, manganese borate, or calcium borate. The chemical formula TiBO will be used herein to designate titanium borate and analogous compounds such as titanium (III) borate $TiBO_3$. In addition, the chemical formulation also designates the case when titanium (III) borate $TiBO_3$ is treated with hydrogen peroxide to obtain titanium (IV) borate. The inorganic metal compound may have a mass median particle size of less than about 2 µm, and may have a mass median particle size of less than about 1 µm.

The inorganic metal compound can be applied in the dry physical form to the surface of the superabsorbent polymer particles. For this, the superabsorbent polymer particles can be intimately mixed with the finely divided inorganic metal compound. The finely divided inorganic metal compound is usually added at about room temperature to the superabsorbent polymer particles and mixed in until a homogeneous mixture is present. For this purpose, mixing is effected in suitable mixers known in the art, such as fluidized bed mixers, paddle mixers, rotary drum mixers, or twin-worm mixers. The mixing of the superabsorbent polymer particles with the finely divided water-insoluble inorganic metal compound may take place before or after any surface crosslinking, for example during the application of the surface crosslinking agent.

Alternatively, a suspension of a finely divided water-insoluble inorganic metal compounds can be prepared and applied to a particulate water absorbent polymer. The suspension is applied, for example, by spraying. Useful dispersion media for preparing the suspension include water, organic solvents such as alcohols, for example methanol, ethanol, isopropanol, ketones, for example acetone, methyl ethyl ketone, or mixtures of water with the aforementioned organic solvents. Other useful dispersion media include dispersion aids, surfactants, protective colloidals, viscosity modifiers, and other auxiliaries to assist in the preparation of the suspension. The suspension can be applied in conventional reaction mixers or mixing and drying systems as described above at a temperature in the range from room temperature to less than the boiling point of the dispersion medium, preferably at about room temperature. It is appropriate to combine the application of the suspension with a surface crosslinking step by dispersing the finely divided water-insoluble metal salt in the solution of the surface crosslinking agent. Alternatively, the suspension can also be applied before or after the surface crosslinking step. The application of the slurry may be followed by a drying step.

In some aspects, the superabsorbent polymer compositions according to the invention can include from 0% to about 5%, or in the alternative from about 0.01% to about 3%, by weight of the dry superabsorbent polymer composition of silica. Examples of silica include fumed silica, precipitated silica, silicon dioxide, silicic acid, and silicates. In some particular aspects, microscopic noncrystalline silicon dioxide is desirable. Products include SIPERNAT®22S and AEROSIL®200 available from Degussa Corporation, Parsippany, N.J. In some aspects, the particle diameter of the inorganic powder can be 1,000 µm or smaller, such as 100 µm or smaller.

In some aspects, the superabsorbent polymer compositions may also include from 0% to about 30% by weight of the dry superabsorbent polymer composition, such as from about 0.1% to about 5% by weight, of water-soluble polymers based by weight of the dry superabsorbent polymer composition, of partly or completely hydrolyzed polyvinyl acetate, polyvinylpyrrolidone, starch or starch derivatives, polyglycols, polyethylene oxides, polypropylene oxides, or polyacrylic acids.

In some aspects, additional surface additives may optionally be employed with the superabsorbent polymer particles, such as odor-binding substances, such as cyclodextrins, zeolites, inorganic or organic salts, and similar materials; anti-caking additives, flow modification agents, surfactants, viscosity modifiers, and the like. In addition, surface additives may be employed that perform several roles during surface modifications. For example, a single additive may be a surfactant, viscosity modifier, and may react to crosslink polymer chains.

In some aspects, the superabsorbent polymer compositions of the present invention may, after a heat treatment step, be treated with water so that the superabsorbent polymer composition has a water content of up to about 10% by weight of the superabsorbent polymer composition. This water may be added with one or more of the surface additives from above added to the superabsorbent polymer.

The superabsorbent polymer compositions according to the invention are desirably prepared by two methods. The composition can be prepared continuously or discontinuously in a large-scale industrial manner, the after-crosslinking according to the invention being carried out accordingly.

According to one method, the partially neutralized monomer, such as acrylic acid, is converted into a gel by free-radical polymerization in aqueous solution in the presence of crosslinking agents and any further components, and the gel is comminuted, dried, ground, and sieved off to the desired particle size. This polymerization can be carried out continuously or discontinuously. For the present invention, the size of the high-capacity superabsorbent polymer composition particles is dependent on manufacturing processes including milling and sieving. It is well known to those skilled in the art that particle size distribution of the superabsorbent polymer particles resembles a normal distribution or a bell shaped curve. It is also known that for various reasons, the normal distribution of the particle size distribution may be skewed in either direction.

The superabsorbent polymer particles of the present invention generally include particle sizes ranging from about 50 to about 1000 µm, or from about 150 to about 850 µm. The present invention may include at least about 40 wt % of the particles having a particle size from about 300 µm to about 600 µm, at least about 50 wt % of the particles having a particle size from about 300 µm to about 600 µm, or at least about 60 wt % of the particles having a particle size from about 300 µm to about 600 µm as measured by screening through a U.S. standard 30 mesh screen and retained on a U.S. standard 50 mesh screen. In addition, the size distribution of the superabsorbent polymer particles of the present invention may include less than about 30% by weight of particles having a size greater than about 600 microns, and less than about 30% by weight of particles having a size of less than about 300 microns as measured using for example a RO-TAP® Mechanical Sieve Shaker Model B available from W. S. Tyler, Inc., Mentor Ohio.

While the form of particles may be used by way of example of the physical form of superabsorbent polymer composition, the invention is not limited to this form and is applicable to other forms such as fibers, foams, films, beads, rods, and the like, as discussed above. In some aspects, when the superabsorbent polymer composition exists as particles or in granule form, it is desirable that these particles have a size of from about 150 µm to about 850 µm based on the sieving process that is well known in the superabsorbent industry.

According to another method, inverse suspension and emulsion polymerization can also be used for preparation of the products according to the invention. According to these processes, an aqueous, partly neutralized solution of monomer, such as acrylic acid, is dispersed in a hydrophobic, organic solvent with the aid of protective colloids and/or emulsifiers, and the polymerization is started by free radical initiators. The internal crosslinking agents may be either dissolved in the monomer solution and are metered in together with this, or are added separately and optionally during the polymerization. The addition of a water-soluble polymer as the graft base optionally takes place via the monomer solution or by direct introduction into the organic solvent. The water is then removed azeotropically from the mixture, and the polymer is filtered off and optionally dried. Internal crosslinking can be carried out by polymerizing-in a polyfunctional crosslinking agent dissolved in the monomer solution and/or by reaction of suitable crosslinking agents with functional groups of the polymer during the polymerization steps.

The result of these methods is a superabsorbent preproduct. A superabsorbent pre-product as used herein is produced by repeating all of the steps for making the superabsorbent, up to and including drying the material, and coarse grinding in a crusher, and removing particles greater than about 850 µm and smaller than about 150 µm.

The superabsorbent polymer composition of the present invention may exhibit certain characteristics, or properties, as measured by Free Swell Gel Bed Permeability (FSGBP), certain whiteness characteristics as measured by Whiteness Index Test, and residual monomer of the superabsorbent polymer composition of the present invention is set forth in the Residual Monoethylenically Unsaturated Monomer Test. The Free Swell Gel Bed Permeability Test is a measurement of the permeability of a swollen bed of superabsorbent material in Darcy (e.g., separate from the absorbent structure) under a confining pressure after what is commonly referred to as "free swell" conditions. In this context, the term "free swell" means that the superabsorbent material is allowed to swell without a swell restraining load upon absorbing test solution as will be described. The superabsorbent polymer compositions of the present invention may have a Free Swell Gel Bed Permeability of about 6 Darcy or more; or about 10 Darcy or more; or about 20 Darcy or more; or from about 6 Darcy to about 200 Darcy; or from about 10 Darcy to about 180 Dacry, or from about 20 to about 160 Darcy.

The superabsorbent polymer composition may have a whiteness index of at least about 7.5 after aging of about 42 days, or a whiteness index of at least about 7.5 after aging of about 49 days, or a whiteness index of at least about 7.5 after aging of about 62 days as measured by the Whiteness Index Test. The superabsorbent polymer composition may have a residual monomer of less than about 200 ppm, or have a monomer of less than about 100 ppm as measured by the Residual Monoethylenically Unsaturated Monomer Test.

The superabsorbent polymer compositions according to the present invention can be employed in many products including sanitary towels, diapers, or wound coverings, and they have the property that they rapidly absorb large amounts of menstrual blood, urine, or other body fluids. Since the agents according to the invention retain the absorbed liquids even under pressure and are also capable of distributing further liquid within the construction in the swollen state, they are more desirably employed in higher concentrations, with respect to the hydrophilic fiber material, such as fluff, when compared to conventional current superabsorbent compositions. They are also suitable for use as a homogeneous superabsorber layer without fluff content within the diaper construction, as a result of which particularly thin articles are possible. The polymers are furthermore suitable for use in hygiene articles (incontinence products) for adults.

The preparation of laminates in the broadest sense, and of extruded and coextruded, wet- and dry-bonded, as well as subsequently bonded structures, are possible as further preparation processes. A combination of these possible processes with one another is also possible.

The superabsorbent polymer compositions according to the invention may also be employed in absorbent articles that are suitable for further uses. In particular, the superabsorbent polymer compositions of this invention can be used in absorbent compositions for absorbents for water or aqueous liquids, desirably in constructions for absorption of body fluids, in foamed and non-foamed sheet-like structures, in packaging materials, in constructions for plant growing, as soil improvement agents, or as active compound carriers. For this, they are processed into a web by mixing with paper or fluff or synthetic fibers or by distributing the superabsorbent polymer composition particles between substrates of paper, fluff, or non-woven textiles, or by processing into carrier materials. They are further suited for use in absorbent compositions such as wound dressings, packaging, agricultural absorbents, food trays and pads, and the like.

The superabsorbent polymer compositions according to the invention show a significant improvement in permeability, i.e. an improvement in the transportation of liquid in the swollen state, while maintaining high absorption and retention capacity, as compared to known superabsorbent polymer compositions.

The present invention may be better understood with reference to the following examples.

Test Procedures

Residual Monoethylenically Unsaturated Monomer Test

The residual monoethylenically unsaturated monomer analysis is carried out using solid film obtained from the polymer solution or superabsorbent composition. By way of example for this test description, the monoethylenically unsaturated monomer is acrylic acid. High performance liquid chromatography (HPLC) with a SPD-10Avp Shimadzu UV detector (available from Shimadzu Scientific Instruments, having a place of business in Columbia, Md., U.S.A) is used to determine the residual acrylic acid monomer content. To determine the residual acrylic acid monomer, about 2.0000+/−0.0010 grams of dry superabsorbent polymer is stirred in a mixture of 88.0 ml of a 0.9% NaCl-solution and 10 ml of 20% aluminum sulfate for 10 minutes using a Ultr-Turrax T25 homogenizer dispersing tool at about 9500 rpm speed. The mixture is filtered with 0.45 micron filter paper and the filtrate is then passed through a Nucleosil C8 120A reverse phase column (available from Column Engineering Incorporated, a business having offices located in Ontario, Calif., U.S.A.) to separate the acrylic acid monomer. The acrylic acid monomer elutes at a certain time with detection limit at about 10 ppm. The peak area of resulting elutes calculated from the chromatogram is then used to calculate the amount of residual acrylic acid monomer in the polymer. Initially, a calibration curve was generated by plotting the response area of pure acrylic acid elutes against its known amount (ppm). A linear curve with a correlation coefficient of greater than 0.996 was obtained.

Whiteness Index Test

The CIE $L^*$, $a^*$, $b^*$ color (D65/10) and opacity (Y) were determined using a ColorFlex® Spectrocolorimeter (commercially available from Hunter Associates Laboratory, Reston, Va.) with 5 mm ring and white ceramic and black glass disks. "$L^*$" represents lightness (100-0), "$a^*$" redness (+) or greenness (−), and "$b^*$" yellowness (+) or blueness (−) of the sample on the CIE $L^*$, $a^*$, $b^*$ scale. This scale is based on the principles described in ASTM E 308 Standard Practice for Computing the Colors of Objects by Using the CIE System. The Whiteness index is calculated by deriving the formula: $=(L^*/b^*)-a^*>7.5$ implies the sample looks white based on physical observation.

Water Content

The amount of water content, measured as "% moisture," can be measured as follows: 1) Weigh 4.5-5.5 grams of superabsorbent polymer composition (SAP) accurately in a pre-weighed aluminum weighing pan; 2) place the SAP and pan into a standard lab oven preheated to 150° C. for 30 minutes; 3) remove and re-weigh the pan and contents; and 4) calculate the percent moisture using the following formula:

% Moisture={((pan wt+initial SAP wt)−(dried SAP & pan wt))*100}/dried SAP wt

Free-Swell Gel Bed Permeability Test (FSGBP)

As used herein, the Free-Swell Gel Bed Permeability Test, also referred to as the Gel Bed Permeability (GBP) Under 0 psi Swell Pressure Test, determines the permeability of a swollen bed of gel particles (e.g., such as the surface treated absorbent material or the superabsorbent material prior to being surface treated), under what is commonly referred to as "free swell" conditions. The term "free swell" means that the gel particles are allowed to swell without a restraining load upon absorbing test solution as will be described. A suitable apparatus for conducting the Gel Bed Permeability Test is shown in FIGS. 1, 2 and 3 and indicated generally as 500. The test apparatus assembly 528 comprises a sample container, generally indicated as 530, and a plunger, generally indicated as 538. The plunger comprises a shaft 538 having a cylinder hole bored down the longitudinal axis and a head 550 positioned at the bottom of the shaft. The shaft hole 562 has a diameter of about 16 mm. The plunger head is attached to the shaft, such as by adhesion. Twelve holes 445 are bored into the radial axis of the shaft, three positioned at every 90 degrees having diameters of about 6.4 mm. The shaft 538 is machined from a LEXAN rod or equivalent material and has an outer diameter of about 2.2 cm and an inner diameter of about 16 mm.

The plunger head 550 has a concentric inner ring of seven holes 560 and an outer ring of 14 holes 554, all holes having a diameter of about 8.8 millimeters as well as a hole of about 16 mm aligned with the shaft. The plunger head 550 is machined from a LEXAN rod or equivalent material and has a height of approximately 16 mm and a diameter sized such that it fits within the cylinder 534 with minimum wall clearance but still slides freely. The total length of the plunger head 550 and shaft 538 is about 8.25 cm, but can be machined at the top of the shaft to obtain the desired mass of the plunger 536. The plunger 536 comprises a 100 mesh stainless steel cloth screen 564 that is biaxially stretched to tautness and attached to the lower end of the plunger 536. The screen is attached to the plunger head 550 using an appropriate solvent that causes the screen to be securely adhered to the plunger head 550. Care must be taken to avoid excess solvent migrating into the open portions of the screen and reducing the open area for liquid flow. Acrylic solvent Weld-on 4 from IPS Corporation (having a place of business in Gardena, Calif., USA) is a suitable solvent.

The sample container 530 comprises a cylinder 534 and a 400 mesh stainless steel cloth screen 566 that is biaxially stretched to tautness and attached to the lower end of the cylinder 534. The screen is attached to the cylinder using an appropriate solvent that causes the screen to be securely adhered to the cylinder. Care must be taken to avoid excess solvent migrating into the open portions of the screen and reducing the open area for liquid flow. Acrylic solvent Weld-on 4 from IPS Corporation (having a place of business in Gardena, Calif., USA) is a suitable solvent. A gel particle sample, indicated as 568 in FIG. 2, is supported on the screen 566 within the cylinder 534 during testing.

The cylinder 534 may be bored from a transparent LEXAN rod or equivalent material, or it may be cut from a LEXAN tubing or equivalent material, and has an inner diameter of about 6 cm (e.g., a cross-sectional area of about 28.27 cm$^2$), a wall thickness of about 0.5 cm and a height of approximately 7.95 cm. A step is machined into the outer diameter of the cylinder 534 such that a region 534a with an outer diameter of 66 mm exists for the bottom 31 mm of the cylinder 534. An o-ring 540 which fits the diameter of region 534a may be placed at the top of the step.

The annular weight 548 has a counter-bored hole about 2.2 cm in diameter and 1.3 cm deep so that it slips freely onto the shaft 538. The annular weight also has a thru-bore 548a of about 16 mm. The annular weight 548 can be made from stainless steel or from other suitable materials resistant to corrosion in the presence of the test solution, which is 0.9 weight percent sodium chloride solution in distilled water. The combined weight of the plunger 536 and annular weight 548 equals approximately 596 grams (g), which corresponds to a pressure applied to the sample 568 of about 0.3 pounds per square inch (psi), or about 20.7 dynes/cm$^2$ (2.07 kPa), over a sample area of about 28.27 cm$^2$.

When the test solution flows through the test apparatus during testing as described below, the sample container 530 generally rests on a weir 600. The purpose of the weir is to divert liquid that overflows the top of the sample container 530 and diverts the overflow liquid to a separate collection device 601. The weir can be positioned above a scale 602 with a beaker 603 resting on it to collect saline solution passing through the swollen sample 568.

To conduct the Gel Bed Permeability Test under "free swell" conditions, the plunger 536, with the weight 548 seated thereon, is placed in an empty sample container 530 and the height from the top of the weight 548 to the bottom of the sample container 530 is measured using a suitable gauge accurate to 0.01 mm. The force the thickness gauge applies during measurement should be as low as possible, preferably less than about 0.74 Newtons. It is important to measure the height of each empty sample container 530, plunger 536, and weight 548 combination and to keep track of which plunger 536 and weight 548 is used when using multiple test apparatus. The same plunger 536 and weight 548 should be used for measurement when the sample 568 is later swollen following saturation. It is also desirable that the base that the sample cup 530 is resting on is level, and the top surface of the weight 548 is parallel to the bottom surface of the sample cup 530.

The sample to be tested is prepared from superabsorbent polymer composition particles which are prescreened through a U.S. standard 30 mesh screen and retained on a U.S. standard 50 mesh screen. As a result, the test sample comprises particles sized in the range of about 300 to about 600 microns. The superabsorbent polymer particles can be prescreened with, for example, a RO-TAP Mechanical Sieve Shaker Model B available from W. S. Tyler, Inc., Mentor Ohio. Sieving is conducted for 10 minutes. Approximately 2.0 grams of the sample is placed in the sample container 530 and spread out evenly on the bottom of the sample container. The container, with 2.0 grams of sample in it, without the plunger 536 and weight 548 therein, is then submerged in the 0.9% saline solution for a time period of about 60 minutes to saturate the sample and allow the sample to swell free of any restraining load. During saturation, the sample cup 530 is set on a mesh located in the liquid reservoir so that the sample cup 530 is raised slightly above the bottom of the liquid reservoir. The mesh does not inhibit the flow of saline solution into the sample cup 530. A suitable mesh can be obtained as part number 7308 from Eagle Supply and Plastic, having a place of business in Appleton, Wis., U.S.A. Saline does not fully cover the superabsorbent polymer composition particles, as would be evidenced by a perfectly flat saline surface in the test cell. Also, saline depth is not allowed to fall so low that the surface within the cell is defined solely by swollen superabsorbent, rather than saline.

At the end of this period, the plunger 536 and weight 548 assembly is placed on the saturated sample 568 in the sample container 530 and then the sample container 530, plunger 536, weight 548, and sample 568 are removed from the solution. After removal and before being measured, the sample container 530, plunger 536, weight 548, and sample 568 are to remain at rest for about 30 seconds on a suitable flat, large grid non-deformable plate of uniform thickness. The thickness of the saturated sample 568 is determined by again measuring the height from the top of the weight 548 to the bottom of the sample container 530, using the same thickness gauge used previously provided that the zero point is unchanged from the initial height measurement. The sample container 530, plunger 536, weight 548, and sample 568 may be placed on a flat, large grid non-deformable plate of uniform thickness that will prevent liquid in the sample container from being released onto a flat surface due to surface tension. The plate has an overall dimension of 7.6 cm by 7.6 cm, and each grid has a cell size dimension of 1.59 cm long by 1.59 cm wide by 1.12 cm deep. A suitable flat, large grid non-deformable plate material is a parabolic diffuser panel, catalogue number 1624K27, available from McMaster Carr Supply Company, having a place of business in Chicago, Ill., U.S.A., which can then be cut to the proper dimensions. This flat, large mesh non-deformable plate must also be present when measuring the height of the initial empty assembly. The height measurement should be made as soon as practicable after the thickness gauge is engaged. The height measurement obtained from measuring the empty sample container 530, plunger 536, and weight 548 is subtracted from the height measurement obtained after saturating the sample 568. The resulting value is the thickness, or height "H" of the swollen sample.

The permeability measurement is initiated by delivering a flow of the 0.9% saline solution into the sample container 530 with the saturated sample 568, plunger 536, and weight 548 inside. The flow rate of test solution into the container is adjusted to cause saline solution to overflow the top of the cylinder 534 thereby resulting in a consistent head pressure equal to the height of the sample container 530. The test solution may be added by any suitable means that is sufficient to ensure a small, but consistent amount of overflow from the top of the cylinder, such as with a metering pump 604. The overflow liquid is diverted into a separate collection device 601. The quantity of solution passing through the sample 568 versus time is measured gravimetrically using the scale 602 and beaker 603. Data points from the scale 602 are collected every second for at least sixty seconds once the overflow has begun. Data collection may be taken manually or with data collection software. The flow rate, Q, through the swollen sample 568 is determined in units of grams/second (g/s) by a linear least-square fit of fluid passing through the sample 568 (in grams) versus time (in seconds).

Permeability in cm² is obtained by the following equation: $K=[Q*H*\mu]/[A*\rho*P]$, where K=Permeability (cm²), Q=flow rate (g/sec), H=height of swollen sample (cm), $\mu$=liquid viscosity (poise) (approximately one centipoise for the test solution used with this Test), A=cross-sectional area for liquid flow (28.27 cm² for the sample container used with this Test), $\rho$=liquid density (g/cm³) (approximately one g/cm³, for the test solution used with this Test) and P=hydrostatic pressure (dynes/cm²) (normally approximately 7,797 dynes/cm²). The hydrostatic pressure is calculated from $P=\rho*g*h$, where $\rho$=liquid density (g/cm³), g=gravitational acceleration, nominally 981 cm/sec², and h=fluid height, e.g., 7.95 cm for the Gel Bed Permeability Test described herein.

A minimum of two samples is tested and the results are averaged to determine the gel bed permeability of the sample.

EXAMPLES

The following examples and preproducts for the examples are provided to illustrate the invention and do not limit the scope of the claims. Unless otherwise stated all parts, and percentages are by weight.

Preproduct A [A Typical Preparative Procedure]

Into a polyethylene vessel equipped with an agitator and cooling coils was added, 25.0 kg of 50% NaOH to 37 kg of distilled water and cooled to 20° C. 9.6 kg of glacial acrylic acid was then added to the caustic solution and the solution again cooled to 20° C. 47.8 g of polyethylene glycol monoallyether acrylate, 47.8 g of ethoxylated trimethylol propane triacrylate SARTOMER® 454 product, and 19.2 kg of glacial acrylic acid were added to the first solution, followed by cooling to 4-6° C. Nitrogen was bubbled through the monomer solution for about 10 minutes. The monomer solution was then discharged in 7.7 kg batches into rectangular trays. To each batch 80 g of 1% by weight of $H_2O_2$ aqueous solution, 120 g of 2 wt % aqueous sodium persulfate solution, and 72 g of 0.5 wt % aqueous sodium erythorbate solution was added homogeneously into the monomer solution stream by injection of the sodium erythorbate solution into the stream of the monomer solution being conveyed from the monomer tank into a tray. The initiated monomer was allowed to polymerize for 20 minutes. The resulting hydrogel was chopped and extruded with a Hobart 4M6 commercial extruder, followed by drying in a Procter & Schwartz Model 062 forced air oven at 175° C. for 10 minutes with up flow and 6 minutes with down flow air on a 20 in×40 in perforated metal tray to a final product moisture level of less than 5 wt %. The dried material was coarse-ground in a Prodeva Model 315-S crusher, milled in an MPI 666-F three-stage roller mill and sieved with an Minox MTS 600DS3V to remove particles greater than 850 µm and smaller than 150 µm.

Examples 1-8

Preproduct A was coated with 1 wt % ethylene carbonate and 4 wt % water using a 20 wt % aqueous solution and the amount of Antioxidant and Chelating Agent set forth in Table 1. The coated Preproduct A was then heated in a convection oven at 190° C. for 45 minutes. The surface crosslinked particulate material was then post treated with 1000 ppm polyethylene glycol 8000 (polyethylene glycol with average molecular weight of 8000) and 5% water.

TABLE 1

Examples 1-8

| Sample | Thermal Initiator, NaPS ppm | Anti-Oxidant | Amount of Anti-oxidant Wt % | Chelating Agent Wt % | Whiteness Index[1,2] | Residual Monomer ppm | Free Swell GBP Darcy |
|---|---|---|---|---|---|---|---|
| Ex 1 206-55-5 | 300 | Bruggolite ®FF6 | 1 | 0 | 9.90 | 170 | 105.82 |
| Ex 2 206-55-2 | 300 | Bruggolite ®FF7 | 1 | 0 | 7.88 | 613 | 26.71 |
| Ex 3 206-65-1 | 300 | Bruggolite ®FF6 | 1 | 0.5 | 7.60 | 499 | 34.25 |
| Ex 4 206-65-7 | 300 | Bruggolite ®FF7 | 1 | 0.5 | 9.39 |  | 48.49 |
| Ex 5 206-75-1 | 100 | Bruggolite ®FF7 | 1 | 0 | 12.48 | 614 | 65.78 |
| Ex 6 196-62-2 | 80 | Bruggolite ®FF6 | 0.11 | 0 | 15.37 | 540 | 28.96 |
| Ex 7 196-63-1 | 75 | Bruggolite ®FF6 | 0.5 | 0 | 12.57 | 67 | 6.18 |
| Ex 8 196-63-2 | 75 | Bruggolite ®FF6 | 1.0 | 0 | 10.80 | 49 | 6.83 |

[1]Whiteness Index = (L/b) − a > 7.5 = Sample looks white
Where, L− = Dark, L+ = White
b− = Blue, b+ = Yellow
a− = Green, a+ = Red
[2]Aged 12 weeks at 40° C., 80% Relative Humidity Preproduct B The chopped hydrogel after the extruder described above in base polymer, A, preparation was sprayed with a 10% aqueous solution of Bruggolite®FF6. The coated hydrogel was dried and ground to particles by similar methods as described in Preproduct A.

Examples 9-10

Preproduct B was coated with 1 wt % ethylene carbonate and 4 wt % water using a 20 wt % aqueous solution. The coated Preproduct B was then heated in a convection oven at 190° C. for 30 minutes. The surface crosslinked particulate material was then post treated with 1000 ppm polyethylene glycol 8000 (polyethylene glycol with average molecular weight of 8000) and 5% water.

TABLE 2

Examples 9-10

| Sample | Thermal Initiator, NaPS ppm | Anti-Oxidant | Amount of Anti-oxidant Wt % | Whiteness Index[1] | Residual Monomer ppm | Free Swell GBP Darcy |
|---|---|---|---|---|---|---|
| Ex 9 206-91-1 | 300 | Bruggolite®FF6 | 1 | 9.73 | 110 | 63.22 |
| Ex 10 206-91-2 | 300 | Bruggolite®FF7 | 1 | 8.28 | 727 | 42.77 |

[1]Aged 10 weeks at 40° C., 80% Relative Humidity

Examples 11-14

About 200 g of dry particulate polymer from Preproduct A was sprayed with a 50 g of aqueous solution containing various amounts of sodium hydrogen sulfite, NaHSO$_3$ (ACS Reagent Grade from Sigma-Aldrich, Product Number: 243973) in a Kitchen Aid mixer set at the lowest speed by an atomizer. The wet polymer was dried in a convection oven at 176° C. for 30 minutes. The dried sample was then milled using a Brinkmann-Retsch Mill. The coated ground polymer was then sieved between 20 and 100 mesh size screens.

Each sample treated with NaHSO$_3$ was then surface cross-linked by spraying with 1 wt % ethylene carbonate and 4 wt % water using a 20 wt % aqueous solution followed by heating in a convection oven at 190° C. for 30 minutes. The surface cross-linked particulate material was then post treated with 1000 ppm polyethylene glycol 8000 (polyethylene glycol with average molecular weight of 8000) and 5% water.

TABLE 3

Examples 11-14

| Sample | Thermal Initiator, NaPS ppm | Anti-Oxidant | Amount of Anti-oxidant Wt % | Whiteness Index[1] | Residual Monomer ppm | Free Swell GBP Darcy |
|---|---|---|---|---|---|---|
| Ex 11 196-66-2 | 300 | Sodium Hydrogen Sulfite, NaHSO$_3$ | 0.1 | 22.16 | 188 | 56.65 |
| Ex 12 196-66-3 | 300 | Sodium Hydrogen Sulfite, NaHSO$_3$ | 0.25 | 22.10 | 110 | 18.66 |
| Ex 13 196-66-4 | 300 | Sodium Hydrogen Sulfite, NaHSO$_3$ | 0.50 | 16.45 | 74 | 29.38 |
| Ex 14 196-66-5 | 300 | Sodium Hydrogen Sulfite, NaHSO$_3$ | 1.0 | 13.36 | 78 | 30.73 |

[1]Aged 6 weeks at 40° C., 80% Relative Humidity

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

What is claimed is:

1. A sanitary article comprising a superabsorbent polymer composition comprising a superabsorbent polymer comprising:
    a) from about 55% to about 99.9% by weight of the superabsorbent polymer of polymerizable unsaturated acid group containing monomer based on the superabsorbent polymer; and
    b) from about 0.001% to about 5% by weight of internal crosslinking agent based on the polymerizable unsaturated acid group containing monomer;
    c) from about 50 to 1000 ppm of a thermal initiator based on the polymerizable unsaturated acid group containing monomer;
    wherein the superabsorbent polymer has a degree of neutralization of greater than about 25%; wherein elements a), b) and c) are polymerized into a crosslinked hydrogel, which is then prepared into superabsorbent polymer particles; the superabsorbent polymer composition further comprising of the following surface additives to form superabsorbent polymer composition particles
        i) from about 0.001% to about 5% by weight of surface crosslinking agent based on the superabsorbent polymer composition; and
        ii) from about 0.01% to about 5% by weight of an antioxidant based on the superabsorbent polymer composition is added to the polymerized product whether in crosslinked hydrogel or subsequent superabsorbent polymer particles or superabsorbent polymer composition particle form, wherein the antioxidant is selected from the group consisting of a sulfinic acid, 2-hydroxy-2-sulfinatoacetic acid, 2-hydroxy-2-sulfonatoacetic acid, sulfamic acid, and sulfonic acid, and salts and derivatives of the foregoing and mixtures thereof, iii) from about 0.01% to about 0.5% by weight of a thermoplastic polymer based on the superabsorbent polymer composition wherein the thermoplastic polymer is selected from the group consisting of polyolefin, polyethylene, styrene polybutadiene, linear low density polyethylene (LLDPE), ethylene acrylic acid copolymer (EAA), ethylene alkyl methacrylate copolymer (EMA), polypropylene (PP), maleated polypropylene, ethylene vinyl acetate copolymer (EVA), polyester, polyamide, and blends of all families of polyolefins, and wherein the superabsorbent polymer composition has a free swell gel bed permeability of at least about 6 Darcy as measured by the Free Swell Gel Bed Permeability Test.

2. The sanitary article according to claim 1 wherein the superabsorbent polymer composition, after storage for 49 days at 40° C. and 80% relative humidity, exhibits a Whiteness Index of at least about 7.5 as measured by the Whiteness Index Test.

3. The sanitary article according to claim 1 wherein the thermal initiator comprises sodium persulfate.

4. The sanitary article according to claim 1 wherein the surface additives further consist of iv) from about 0.001% to about 0.5% by weight of polyethylene glycol coating based on the superabsorbent polymer composition.

5. The sanitary article according to claim 1 wherein the surface additives further consist of v) from about 0.01% to about 0.5% by weight of polyvinyl amine based on the superabsorbent polymer composition.

6. The sanitary article of claim 1 wherein the thermoplastic polymer comprises a maleated polypropylene.

7. The sanitary article of claim 1 wherein at least about 50% by weight of the superabsorbent polymer composition have a particle size from about 300 µm to about 600 µm.

8. The sanitary article of claim 1 wherein the sanitary article is a diaper.

9. A superabsorbent polymer composition comprising a superabsorbent polymer composition comprising superabsorbent polymer particles surface treated with i) from about 0.01% to about 0.5% by weight of a thermoplastic polymer based on the superabsorbent polymer composition wherein the thermoplastic coating is selected from the group consisting of polyolefin, polyethylene, styrene polybutadiene, linear low density polyethylene (LLDPE), ethylene acrylic acid copolymer (EAA), ethylene alkyl methacrylate copolymer (EMA), polypropylene (PP), maleated polypropylene, ethylene vinyl acetate copolymer (EVA), polyester, polyamide, and blends of all families of polyolefins; and ii) from about 0.01% to about 5% by weight of an antioxidant based on the superabsorbent polymer composition wherein the antioxidant is added to the polymerized product whether in crosslinked hydrogel or subsequent superabsorbent polymer particles or superabsorbent polymer composition particle form, wherein the antioxidant is selected from a sulfinic acid, 2-hydroxy-2-sulfinatoacetic acid, 2-hydroxy-2-sulfonatoacetic acid, sulfamic acid, and sulfonic acid, and salts and derivatives of the foregoing.

10. The superabsorbent polymer composition according to claim 9 wherein the superabsorbent polymer composition, after storage for 84 days at 40° C. and 80% relative humidity, exhibits a Whiteness Index of at least about 7.5 as measured by the Whiteness Index Test.

11. The superabsorbent polymer composition according to claim 9 further comprises iii) from about 0.001% to about 0.5% by weight of a polyethylene glycol coating based on the superabsorbent polymer composition.

12. The superabsorbent polymer composition according to claim 9 further comprises iv) from about 0.01% to about 2% by weight of a water-insoluble inorganic metal compound, based on the superabsorbent polymer composition.

13. The superabsorbent polymer composition according to claim 12 wherein the water-insoluble inorganic metal compound comprises aluminum phosphate.

14. The superabsorbent polymer composition according to claim 9 further comprises v) from about 0.01% to about 2% by weight of a water-insoluble inorganic metal compound, based on the superabsorbent polymer composition.

15. The superabsorbent polymer composition according to claim 14 wherein the water-insoluble inorganic metal compound comprises aluminum phosphate.

16. The superabsorbent polymer composition of claim 9 further comprising vi) from 0.01% to about 5% by weight of a multivalent metal salt, based on the superabsorbent polymer composition.

17. The superabsorbent polymer composition of claim 16 wherein the multivalent metal salt is selected from aluminum sulfate or aluminum lactate.

18. The superabsorbent polymer composition of claim 9 further comprising vii) from about 0.01% to about 0.5% by weight of polyvinyl amine based on the superabsorbent polymer composition.

19. The superabsorbent polymer composition according to claim 9 wherein the superabsorbent polymer composition comprises a residual monomer content of less than about 200 ppm as measured by the Residual Monoethylenically Unsaturated Monomer Test.

20. A sanitary article comprising the superabsorbent polymer of claim 9.

21. A sanitary article of claim 20 wherein the sanitary article is a diaper.

* * * * *